(12) United States Patent
Sinha et al.

(10) Patent No.: US 9,567,390 B2
(45) Date of Patent: Feb. 14, 2017

(54) HUMANIZED HIGH AFFINITY RECOMBINANT ANTIBODY AGAINST HEPATITIS B SURFACE ANTIGEN

(75) Inventors: Subrata Sinha, New Delhi (IN); Ashutosh Tiwari, New Delhi (IN); Navin Khanna, New Delhi (IN); Subrat K. Acharya, New Delhi (IN)

(73) Assignees: Department of Biotechnology, New Delhi (IN); All India Institute of Medical Sciences, New Delhi (IN); International Center for Genetic and Biotechnology, New Delhi (IN)

( * ) Notice: Subject to any disclaimer, the term of this patent is extended or adjusted under 35 U.S.C. 154(b) by 1502 days.

(21) Appl. No.: 12/865,623

(22) PCT Filed: Dec. 2, 2008

(86) PCT No.: PCT/IN2008/000796
§ 371 (c)(1),
(2), (4) Date: Nov. 4, 2010

(87) PCT Pub. No.: WO2009/093263
PCT Pub. Date: Jul. 30, 2009

(65) Prior Publication Data
US 2011/0046354 A1 Feb. 24, 2011

(30) Foreign Application Priority Data
Jan. 23, 2008 (IN) .................. 190/DEL/08

(51) Int. Cl.
*C07K 16/00* (2006.01)
*C07K 16/08* (2006.01)

(52) U.S. Cl.
CPC ......... *C07K 16/082* (2013.01); *C07K 2317/24* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS 5,530,101 A * 6/1996 Queen et al. ............. 530/387.3

FOREIGN PATENT DOCUMENTS

WO  WO2009082781  * 7/2009

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Bose et al. (Molecular Immunology, vol. 40, pp. 617-631, 2003).*
Bose B. et al.: Characterization and molecular modeling of a highly stable anti-Hepatitis B surface antigen scFv Mol. Immunol., vol. 40, No. 9, Dec. 2003 (Dec. 2003), pp. 617-631.
Roguska M.A. et al.: Humanization of murine monoclonal antibodies through variable domain resurfacing. Proc Natl Acad Sci USA, vol. 91, No. 3, Feb. 1, 1994 (Feb. 1, 1994), pp. 969-973.
Heijtink RA, Kruining J, Weber YA, De Man RA. Schaim SW. Anti-hepatitis B virus activity of a mixture of two monoclonal antibodies in an "inhibition in solution" assay. Hepatology. Oct. 1995; 22(4 Pt 1): 1078-83.
Shouval D, Wands Jr, Zurawski VR Jr. Isselbacher KJ, Shafritz DA. Selecting binding and complement-mediated lysis of human hepatoma cells (PLC /PRF/ 5) in culture by monoclonal antibodies to hepatitis B surface antigen. Proc Natl Acad Sci U S A. Jan. 1982; 79 (2): 650-4.
Shin YW, Ryoo KH, Hong KW, Chang KH, Choi JS, So M, Kim PK, Park JY, Bong KT, Kimsh. Human monoclonal antibody against Hepatitis B virus surface antigen (HbsAg). Antiviral Res. Aug. 2007; 75 (2): 113-20.
Genbank Accession: CAD70712, Version CAD70712.1 GI:28950508, "anti-HBsAg ScFv antibody [synthetic construct]" Nov. 21, 2003 (Nov. 21, 2003). [DB Source: embl accession AJ549501.1] (Whole Document).
Falero G. Rodraguez 1, Sarracent J. Otero AJ, Rodraguez BL, Rojas A, Ochoa E. Generation of murine triomas secreting bi-specific monoclonal antibodies thatrecognize HbsAG ad and ay subtypes. Hybridoma. Dec. 1992; 11 (6):815-23.
Shearer MH, Sureau C, Dunbar B, Kennedy RC. Structural characterization of viral neutralizing monoclonal antibodies to hepatitis B surface antigen. Mol immunol. Dec. 1998;35(18): 1149-60.
Maeda F, Nagatsuka Y, Lhara S, Aotsuka S, Ono Y, Inoko H, Takekoshi M. Bacterial expression of a human recombinant monoclonal antibody fab fragment against hepatitis B surface antigen. J Med Virol. Aug. 1999;58 (4):338-45.
Lohman KL, Kieber-Emmons T, Kennedy RC. Molecular characterization and structural modeling of immunoglobulin variable regions form murine monoclonal antibodies specific for hepatitis B virus surface antigen. Mol Immunol. Oct. 1993;30(14): 1295-306.
Heijtink RA, Kruining J, Van Bergen P, De Rave S, Van Hattum J. Schutten M, Osterhaus AD. Characterization of a human monoclonal antibody obtained after immunization with plasma vaccine and a booster with recombinant-DNA hepatitis B vaccine. J Med Virol. Mar. 2002;66(3):304-I I.

(Continued)

*Primary Examiner* — Laura B Goddard
*Assistant Examiner* — Meera Natarajan
(74) *Attorney, Agent, or Firm* — The Webb Law Firm

(57) ABSTRACT

This invention relates to a high affinity recombinant humanized antibody fragment (scFv) specific for hepatitis B surface antigen having unique inter/intra chain bonding interaction because of 28 altered amino acid residues from the original mouse (5S) antibody and its chimeric Fab form, wherein fine tuning of the vernier zone residue makes it closer to the human sequence without any structural constraints.

11 Claims, 11 Drawing Sheets

(56) References Cited

OTHER PUBLICATIONS

Figure 3:
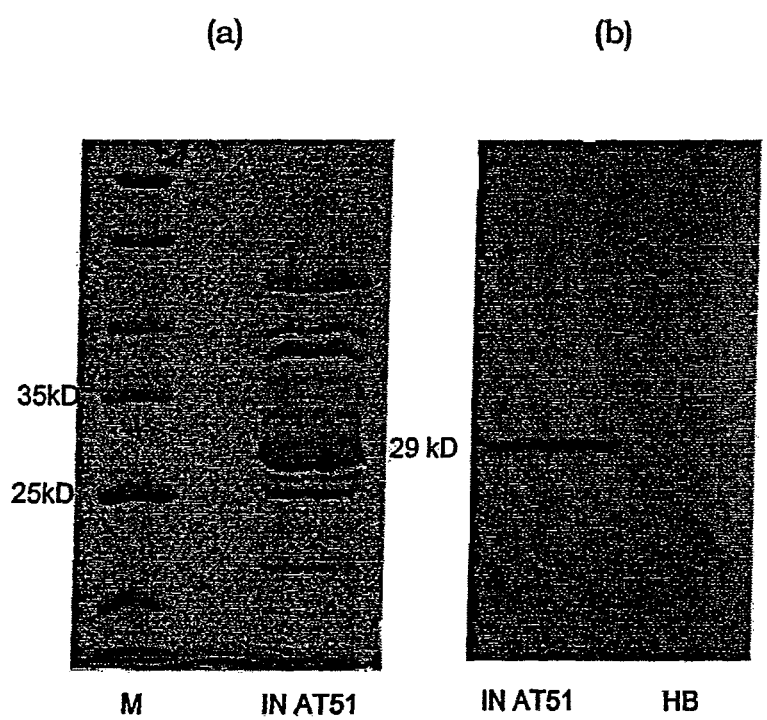

Yano A, Maeda F, Takekoshi M. Transgenic tobacco cells producing the human monoclonal antibody to hepatitis B virus surface antigen. J Med Virol. Jun. 2004; 73(2):208-15.
Desgranges C. Pare J, Pichoud C, Souche S, Frommel D, Trepo C. High affinity human monoclonal antibodies directed against hepatitis B surfaceantigen. J Virol Methods. Jul. 1987; 16 (4):281-92.
Eren R. Lubin 1, Terkieltaub D, Ben-Moshe O, Zauberman A, Uhlma'hn R, Tzahor T, Moss S, Llan E, Shouval D, Galun E, Daudi N, Marcus H, Reisner Y, Dagan S. Human monoclonal antibodies specific to hepatitis B virus generated in a human/ mouse radiation chimera: the Trimera system. Immunology. Feb. 1998;93(2): 154-.
Morrison SL, Johnson MJ, Herzenberg LA, Oi VT. Chimeric human antibody molecules; mouse antigen-binding domains with human constant region domains. Proc Natl Acad Sci U S A. Nov. 1984;81(21):6851-5.
Bose B, Khanna N, Acharys SK5 Sinha S. High affinity mouse—human chimeric Fab against Hepatitis B surface antigen. World J Gastroenterol.Dec. 28, 2005;1 1(48);7569-78.
Bose B, Khanna N, Acharya SK, Sinha S. Generation and characterization of a high-affinity chimaeric antibody against hepatitis B surface antien. Biotechnol Appl Biochem.Feb. 2006;43(Pt2):93-101.
Khazaeli MB, Saleh MN, Liu TP, Meredith RF, Wheeler RH, Baker TS, King D, Secher D, Allen L, Rogers K, et al. Pharmacokinetics and immune response of 131l-chimeric mouse/human B72.3 (human gamma 4) monoclonal antibody in humans. Cancer Res. Oct. 15, 1991;51 (20): 5461-6.

* cited by examiner

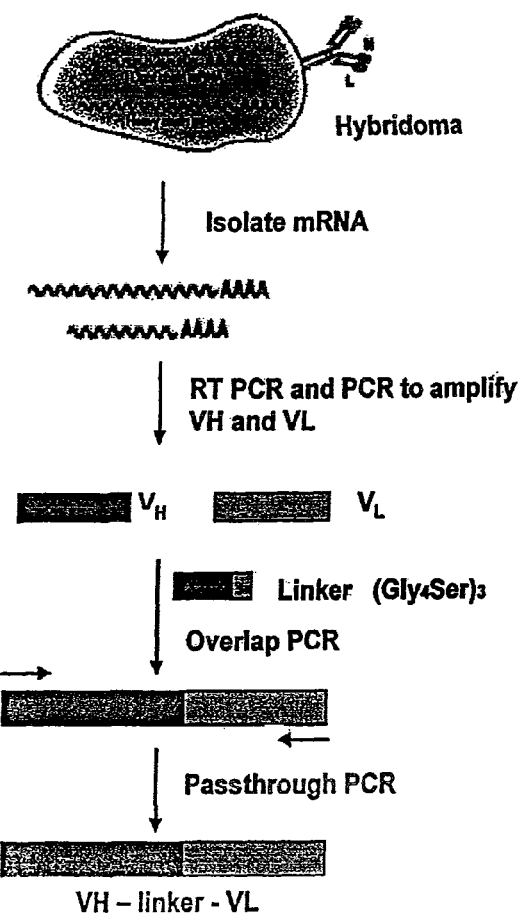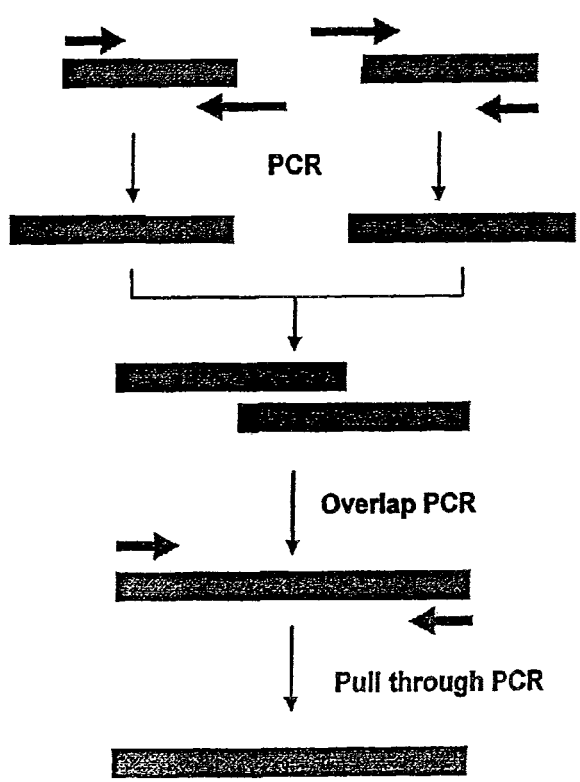
Figure.1
Figure.2

(a)

```
                         CDR H1
5S Mouse VH    EVQLQQPGAELATPGASLKMSCKAS GYSFSTYNIH WVKQTPGRGLEW
Human cons.V_H1  Q---V-S---VKK---V-V-----  ----------  --R-A--Q----
Humanized VH    E---V-S---VAK---V-V-----  ----------  --R-A--Q----

CDR H2
5S Mouse VH    IG TIYPGIGDTSYNQKFKG KATLTADKSSSTAYLHLNSLTSEDSAVYYC
Human cons.V_H1 M- ----------------- RV-I---T-T----ME-S--R---T-----
Humanized VH   I- ----------------- KA-L---K-T----LE-S--R---T-----

CDR H3
5S Mouse VH    AR SDIYYGNYNALDY WGQGTSVTVSS
Human cons.V_H1 -- ------------- -----L-----
Humanized VH   -- ------------- -----L-----
```

(b)

```
                                         CDR L1
5S Mouse VL    IVMTQTPLSLPVSLGDQASISC RASQSIVHSYGDTYLE WHLQKPGQS
Human VLκII    -----S------TP-EP----  ---------------- -Y-------
Humanized VL   -----S------TP-EP----  ---------------- -Y-------

CDR L2
5S Mouse VL    PKLLIY KVSNRFS GVPDRFSGSGSGTEFTLKISRVEAEDLGVYFC FQR
Human VLκII    -Q---  -------  ------------D------------V---Y- ---
Humanized VL   -Q---  -------  ------------D------------V---Y- ---

CDR L3
5S Mouse VL    SYVPWTF GGGTKLELKR
Human VLκII    -------  -Q---V-I--
Humanized VL   -------  -Q---V-I--
```

Figure 11

```
atggcggaagtgcagctggttcagagcggtgcggaagtggcgaaaccgggtgcgagcgtg
 M  A  E  V  Q  L  V  Q  S  G  A  E  V  A  K  P  G  A  S  V
aaagtgagctgcaaagcgagcggctatagctttagcacctataacattcattgggtgcgt
 K  V  S  C  K  A  S  G  Y  S  F  S  T  Y  N  I  H  W  V  R
caggcgccgggtcagggcctggaatggattggcaccatttatccgggcattggcgatacc
 Q  A  P  G  Q  G  L  E  W  I  G  T  I  Y  P  G  I  G  D  T
agctataaccagaaattcaaaggcaaagcgaccctgaccgcggataaaagcaccagcacc
 S  Y  N  Q  K  F  K  G  K  A  T  L  T  A  D  K  S  T  S  T
gcgtatctggaactgagcagcctgcgtagcgaagataccgcggtgtattattgcgcgcgt
 A  Y  L  E  L  S  S  L  R  S  E  D  T  A  V  Y  Y  C  A  R
agcgatatttattacggcaactacaacgcgctggattattggggccagggcaccctggtt
 S  D  I  Y  Y  G  N  Y  N  A  L  D  Y  W  G  Q  G  T  L  V
accgtgagcagcagcggcggtggtagcggtggtggtggcaccggtggtggcggcagcatt
 T  V  S  S  S  G  G  G  S  G  G  G  G  T  G  G  G  S  I
gtgatgacccagtctccgctgagtctgccggttacgccgggtgagccggccagcattagc
 V  M  T  Q  S  P  L  S  L  P  V  T  P  G  E  P  A  S  I  S
tgccgtgcgagccagagcattgtgcatagctatggcgatacctatctggaatggtatctg
 C  R  A  S  Q  S  I  V  H  S  Y  G  D  T  Y  L  E  W  Y  L
cagaaaccgggtcagtctccgcagctgctgatttataaagtgagcaaccgttttagcggc
 Q  K  P  G  Q  S  P  Q  L  L  I  Y  K  V  S  N  R  F  S  G
gtgccggatcgctttagcggcagcggtagtggcaccgattttaccctgaaaattagccgt
 V  P  D  R  F  S  G  S  G  S  G  T  D  F  T  L  K  I  S  R
gtggaagcggaagatgtgggcgtgtattattgttttcagcgtagctatgtgccgtggacc
 V  E  A  E  D  V  G  V  Y  Y  C  F  Q  R  S  Y  V  P  W  T
tttggccagggcaccaaagtggaaattaaacgt
 F  G  Q  G  T  K  V  E  I  K  R
```

Figure 12

SEQUENCE LISTING

```
<160> NUMBER OF SEQ ID NOS: 51

<210> SEQ ID NO 1
<211> LENGTH: 16
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 1

Arg Ala Ser Gln Ser Ile Val His Ser Tyr Gly Asp Thr Tyr Leu Glu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 2

Lys Val Ser Asn Arg Phe Ser
1               5

<210> SEQ ID NO 3
<211> LENGTH: 10
<212> TYPE: PRT
<213> ORGANISM: Artificial Sequence
```

```
<220> FEATURE:
<223> OTHER INFORMATION: Partial amino acid sequence for modified
      recombinant antibody fragment anti-HBs-scFv

<400> SEQUENCE: 3

Phe Gln Arg Ser Tyr Val Pro Trp Thr Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 4

Gly Tyr Ser Phe Ser Thr Tyr Asn Ile His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 5

Thr Ile Tyr Pro Gly Ile Gly Asp Thr Ser Tyr Asn Gln Lys Phe Lys
1               5                   10                  15

Gly

<210> SEQ ID NO 6
<211> LENGTH: 13
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 6

Ser Asp Ile Tyr Tyr Gly Asn Tyr Asn Ala Leu Asp Tyr
1               5                   10

<210> SEQ ID NO 7
<211> LENGTH: 25
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 7

Glu Val Gln Leu Val Gln Ser Gly Ala Glu Val Ala Lys Pro Gly Ala
1               5                   10                  15

Ser Val Lys Val Ser Cys Lys Ala Ser
            20                  25

<210> SEQ ID NO 8
<211> LENGTH: 14
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv
```

<400> SEQUENCE: 8

Trp Val Arg Gln Ala Pro Gly Gln Gly Leu Glu Trp Ile Gly
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 9

Lys Ala Thr Leu Thr Ala Asp Lys Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 10
<211> LENGTH: 9
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 10

Trp Gly Gln Gly Th

```
1               5                  10                  15
Leu Lys Ile Ser Arg Val Glu Ala Glu Asp Val Gly Val Tyr Tyr Cys
            20                  25                  30
```

<210> SEQ ID NO 14
<211> LENGTH: 10
<212> TYPE: PRT
<213> ORGANISM: Artificial Sequence
<220> FEATURE:
<223> OTHER INFORMATION: Partial amino acid sequence for modified
      recombinant antibody fragment anti-HBs-scFv

<400> SEQUENCE: 14

```
Gly Gln Gly Thr Lys Val Glu Ile Lys Arg
1               5                  10
```

<210> SEQ ID NO 15
<211> LENGTH: 753
<212> TYPE: DNA
<213> ORGANISM: Artificial Sequence
<220> FEATURE:
<223> OTHER INFORMATION: Nucleotide sequence for modified recombinant
      antibody fragment anti-HBs-scFv

<400> SEQUENCE: 15

```
atggcggaag tgcagctggt tcagagcggt gcggaagtgg cgaaaccggg tgcgagcgtg      60
aaagtgagct gcaaagcgag cggctatagc tttagcacct ataacattca ttgggtgcgt     120
caggcgccgg gtcagggcct ggaatggatt ggcaccattt atccgggcat tggcgatacc     180
agctataacc agaaattcaa aggcaaagcg accctgaccg cggataaaag caccagcacc     240
gcgtatctgg aactgagcag cctgcgtagc gaagataccg cggtgtatta ttgcgcgcgt     300
agcgatattt attacggcaa ctacaacgcg ctggattatt ggggccaggg caccctggtt     360
accgtgagca gcagcggcgg tggtagcggt ggtggtggca ccggtggtgg cggcagcatt     420
gtgatgaccc agtctccgct gagtctgccg gttacgccgg gtgagccggc cagcattagc     480
tgccgtgcga gccagagcat tgtgcatagc tatggcgata cctatctgga atggtatctg     540
cagaaaccgg gtcagtctcc gcagctgctg atttataaag tgagcaaccg tttttagcggc     600 gtgccggatc gctttagcgg cagcggtagt ggcaccgatt ttaccctgaa aattagccgt     660
gtggaagcgg aagatgtggg cgtgtattat tgttttcagc gtagctatgt gccgtggacc     720
tttggccagg gcaccaaagt ggaaattaaa cgt                                   753
```

<210> SEQ ID NO 16
<211> LENGTH: 251
<212> TYPE: PRT
<213> ORGANISM: Artificial Sequence
<220> FEATURE:
<223> OTHER INFORMATION: Nucleotide sequence for modified recombinant
      antibody fragment anti-HBs-scFv

<400> SEQUENCE: 16

```
Met Ala Glu Val Gln Leu Val Gln Ser Gly Ala Glu Val Ala Lys Pro
1               5                  10                  15

Gly Ala Ser Val Lys Val Ser Cys Lys Ala Ser Gly Tyr Ser Phe Ser
            20                  25                  30

Thr Tyr Asn Ile His Trp Val Arg Gln Ala Pro Gly Gln Gly Leu Glu
        35                  40                  45

Trp Ile Gly Thr Ile Tyr Pro Gly Ile Gly Asp Thr Ser Tyr Asn Gln
    50                  55                  60
```

```
Lys Phe Lys Gly Lys Ala Thr Leu Thr Ala Asp Lys Ser Thr Ser Thr
 65                  70                  75                  80

Ala Tyr Leu Glu Leu Ser Ser Leu Arg Ser Glu Asp Thr Ala Val Tyr
                 85                  90                  95

Tyr Cys Ala Arg Ser Asp Ile Tyr Tyr Gly Asn Tyr Asn Ala Leu Asp
            100                 105                 110

Tyr Trp Gly Gln Gly Thr Leu Val Thr Val Ser Ser Gly Gly Gly
            115                 120                 125

Ser Gly Gly Gly Gly Thr Gly Gly Gly Ser Ile Val Met Thr Gln
130                 135                 140

Ser Pro Leu Ser Leu Pro Val Thr Pro Gly Glu Pro Ala Ser Ile Ser
145                 150                 155                 160

Cys Arg Ala Ser Gln Ser Ile Val His Ser Tyr Gly Asp Thr Tyr Leu
                165                 170                 175

Glu Trp Tyr Leu Gln Lys Pro Gly Gln Ser Pro Gln Leu Leu Ile Tyr
            180                 185                 190

Lys Val Ser Asn Arg Phe Ser Gly Val Pro Asp Arg Phe Ser Gly Ser
            195                 200                 205

Gly Ser Gly Thr Asp Phe Thr Leu Lys Ile Ser Arg Val Glu Ala Glu
210                 215                 220

Asp Val Gly Val Tyr Tyr Cys Phe Gln Arg Ser Tyr Val Pro Trp Thr
225                 230                 235                 240

Phe Gly Gln Gly Thr Lys Val Glu Ile Lys Arg
                245                 250
```

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
tcgacttgcg cccgcccgtt tkakytccar cttkgtscc                          39

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
tgargagacr gtgactgarg t                                             21

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
attgtgatga cccagact                                                 18

<210> SEQ ID NO 20
<211> LENGTH: 45
<212> TYPE: DNA
<213> ORGANISM: Artificial Sequence
<220> FEATURE:
<223> OTHER INFORMATION: Primer

```
<400> SEQUENCE: 20
gcaactgcgg cccagccggc catggccgag gtgcagctkc agcag                45

<210> SEQ ID NO 21
<211> LENGTH: 42
<212> TYPE: DNA
<213> ORGANISM: Artificial Sequence
<220> FEATURE:
<223> OTHER INFORMATION: Primer

<400> SEQUENCE: 21
ggtggtggtg ggagcggtgg tggcactggc ggcggcggat ct                   42

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
tcagtcacyg tctcytcagg tggtggtggg agc                             33

<210> SEQ ID NO 23
<211> LENGTH: 32
<212> TYPE: DNA
<213> ORGANISM: Artificial Sequence
<220> FEATURE:
<223> OTHER INFORMATION: Primer

<400> SEQUENCE: 23
gtctgggtca tcacaataga tccgccgccg cc                              32

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
ggtgcagctg caggtgcccg gggctgag                                   28

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
gcagctgcag cagagcgggg ctgagc                                     26

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
ggggctgagg tggcgacgcc tgg                                        23

<210> SEQ ID NO 27
```

```
<211> LENGTH: 26
<212> TYPE: DNA
<213> ORGANISM: Artificial Sequence
<220> FEATURE:
<223> OTHER INFORMATION: Primer

<400> SEQUENCE: 27
gctgagctgg cgaagcctgg ggcctc                                          26

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
ctggggcctc agtgaagatg tcctgcaag                                       29

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
ggcctcagtg aaggtgtcct gcaagg                                          26

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
cactgggtac ggcagacacc tgg                                             23

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
ggtacggcag gcacctggac gggg                                            24

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
ggcacctgga cagggcctgg aatg                                            24

<210> SEQ ID NO 33
<211> LENGTH: 33
<212> TYPE: DNA
<213> ORGANISM: Artificial Sequence
<220> FEATURE:
<223> OTHER INFORMATION: Primer

<400> SEQUENCE: 33
```

-continued ctgcagacaa atccaccagc acagcctatt tgc        33

<210> SEQ ID NO 34
<211> LENGTH: 39
<212> TYPE: DNA
<213> ORGANISM: Artificial Sequence
<220> FEATURE:
<223> OTHER INFORMATION: Primer

<400> SEQUENCE: 34
ctccaacaca gcctatttgg aactcaacag cctgacatc        39

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
cctatttgga actcagcagc ctgacatctg        30

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
cagcagcctg agatctgagg actc        24

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
gacatctgag gacaccgcgg tctattactg        30

<210> SEQ ID NO 38
<211> LENGTH: 29
<212> TYPE: DNA
<213> ORGANISM: Artificial Sequence
<220> FEATURE:
<223> OTHER INFORMATION: Primer

<400> SEQUENCE: 38
ggtcaaggaa ccctggtcac tgtctcttc        29

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
gtgatgaccc agagtccact ctccc        25

<210> SEQ ID NO 40
<211> LENGTH: 28
<212> TYPE: DNA

```
<213> ORGANISM: Artificial Sequence
<220> FEATURE:
<223> OTHER INFORMATION: Primer

<400> SEQUENCE: 40
ccctgcctgt caccctTGGA gatcaagc                                              28

<210> SEQ ID NO 41
<211> LENGTH: 29
<212> TYPE: DNA
<213> ORGANISM: Artificial Sequence
<220> FEATURE:
<223> OTHER INFORMATION: Primer

<400> SEQUENCE: 41
cctgcctgtc accccgggag aacaagcct                                             29

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
ctgtcaccct tggagaacaa gcctccatct c                                          31

<210> SEQ ID NO 43
<211> LENGTH: 29
<212> TYPE: DNA
<213> ORGANISM: Artificial Sequence
<220> FEATURE:
<223> OTHER INFORMATION: Primer

<400> SEQUENCE: 43
caccccggga gaaccggcct ccatctctt                                             29

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
cctatttgga atggtacctg cagaaaccag                                            30

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
ggccagtctc cacagctcct gatctac                                               27

<210> SEQ ID NO 46
<211> LENGTH: 29
<212> TYPE: DNA
<213> ORGANISM: Artificial Sequence
<220> FEATURE:
<223> OTHER INFORMATION: Primer

<400> SEQUENCE: 46
gtggatcagg gacagatttc acactcaag                                             29
```

```
<210> SEQ ID NO 47
<211> LENGTH: 29
<212> TYPE: DNA
<213> ORGANISM: Artificial Sequence
<220> FEATURE:
<223> OTHER INFORMATION: Primer

<400> SEQUENCE: 47
ggaggcacca aggtggaact caaacgggc                                       29

<210> SEQ ID NO 48
<211> LENGTH: 32
<212> TYPE: DNA
<213> ORGANISM: Artificial Sequence
<220> FEATURE:
<223> OTHER INFORMATION: Primer

<400> SEQUENCE: 48
gatgtgggag tttattactg ctttcaacgt tc                                   32

<210> SEQ ID NO 49
<211> LENGTH: 28
<212> TYPE: DNA
<213> ORGANISM: Artificial Sequence
<220> FEATURE:
<223> OTHER INFORMATION: Primer

<400> SEQUENCE: 49
gtggacgttc ggtcaaggca ccaagctg                                        28

<210> SEQ ID NO 50
<211> LENGTH: 29
<212> TYPE: DNA
<213> ORGANISM: Artificial Sequence
<220> FEATURE:
<223> OTHER INFORMATION: Primer

<400> SEQUENCE: 50
ggaggcacca aggtggaact caaacgggc                                       29

<210> SEQ ID NO 51
<211> LENGTH: 27
<212> TYPE: DNA
<213> ORGANISM: Artificial Sequence
<220> FEATURE:
<223> OTHER INFORMATION: Primer

<400> SEQUENCE: 51
gcaccaaggt ggaaatcaaa cgggcgg                                         27
```

HUMANIZED HIGH AFFINITY RECOMBINANT ANTIBODY AGAINST HEPATITIS B SURFACE ANTIGEN

The Sequence Listing associated with this application is filed in electronic format via EFS-Web and is hereby incorporated by reference into the specification in its entirety. The name of the text file containing the Sequence Listing is 102256_ST25.txt. The size of the text file is 14,813 bytes, and the text file was created on Jul. 12, 2013.

FIELD OF INVENTION

The present invention relates to the generation of high affinity humanized antibody fragment (scFv) against hepatitis B surface antigen for the treatment or prevention of hepatitis B infection.

BACKGROUND OF INVENTION

HBV (Hepatitis B virus) is a major cause of acute and chronic hepatitis worldwide. Prevention of HBV infection may be achieved with active or passive immunization. Active immunization with recombinant HBV vaccines can prevent HBV infection if given before exposure. Despite the introduction of universal vaccination against hepatitis B in around 100 countries, persistent HBV infection is still a serious problem, with an estimated worldwide death rate of one million people per year. Protective antibodies that appear after natural infection are mostly directed against the major antigenic 'a' determinant of hepatitis B surface antigen (HBsAg). The immunodominant 'a' epitope is present in all serotypes. Antibodies against HBsAg are thus advocated for passive immunotherapy for managing chronic viral infection. Passive immunization with hepatitis B specific antibodies, given shortly after exposure, can decrease the incidence or severity of disease.

Currently, Hepatitis B immune globulin (HBIG), collected from the blood of hyper immune human donors, is used for the post-exposure prophylaxis in cases of accidental needle stick injuries, liver transplant patients and for the prevention of vertical transfer of HBV infection form mother to child. This blood-derived product is not manufactured in India. However, such blood-derived products are costly and can cause cross contamination. Therefore, recombinant antibodies can be good substitutes for human serum antibodies.

Inventors developed a mouse monoclonal antibody (5S) against the 'a' epitope of the hepatitis B surface antigen (HBsAg). However such mouse antibodies often induce a significant human anti mouse antibody (HAMA) response when administered to patients and thus limiting their potential use for human therapy, especially when repeated administration is necessary. HAMA greatly reduces the in-vivo efficacy of mouse antibodies. Moreover, the half-life of a mouse antibody in human plasma is shorter compared with that of human antibody. Several recombinant anti-HbsAg antibody fragments have been reported in literature.

However most of them are of mouse origin and are not available for therapeutic purposes (1-15). To reduce the immunogenicity of murine antibodies, chimeric antibodies were constructed, which combine the variable region of a mouse antibody with a human antibody constant region, thus retaining the binding specificity of murine antibody while presenting less foreign amino acid sequence to the human immune system (16). Inventors also generated chimeric antibody against HBsAg (17-18). Some of the chimeric antibodies have proved less immunogenic in humans, whereas others are almost as immunogenic as murine antibodies. Moreover, in an animal study to evaluate the immunogenicity of chimeric antibodies, it was found that the anti-variable domain response was not attenuated in the chimeric antibodies, suggesting that the murine variable domain can still lead to a significant human anti mouse antibody (HAMA) response (19). Therefore, for therapeutic purposes it may be necessary to fully humanize a murine antibody by altering the variable domain to make them human like. It is well established that humanization of mouse antibody is desirable to reduce its potential product immunogenicity. However humanization is practical only if it does not reduce or destroy the binding affinity of antibody. Humanized antibodies are safer for therapeutic uses and currently several such humanized antibodies are in clinical uses for various diseases. Although some chimeric antibodies are in clinical use, it is worth noting that most of the antibodies in phase I, II and III clinical trials today are humanized antibodies.

All the mouse/humanized and human anti-HbsAg antibodies reported in literature have unique complementarily determining regions (CDRs) sequence and have unique antigen-antibody interactions which are different form the recombinant molecule of this invention.

1. Ehrlich P H, Moustafa Z A, Justice J C. Harfeldt K E, Kelley R L, Osterg L. Characterization of human monoclonal antibodies directed against hepatitis B surface antigen. Hum Antibodies Hybridomas. 1992 January; 3(1):2-7.
2. Kennedy R C, Ionescu-Matiu I, Adler-Storthz K, Henkel R D Sanchez Y, Dreesman G R. Characterization of anti-hepatitis B surface antigen monoclonal antibodies. Intervirology. 1983; 19(3): 176-80.
3. Heijtink R A, Kruining J, Weber Y A, de Man R A. Schaim S W. Anti-hepatitis B virus activity of a mixture of two monoclonal antibodies in an "inhibition in solution" assay. Hepatology. 1995 October; 22(4 Pt 1): 1078-83.
4. Shouval D, Wands J R, Zurawski V R Jr. Isselbacher K J, Shafritz D A. Selecting binding and complement-mediated lysis of human hepatoma cells (PLC/PRF/5) in culture by monoclonal antibodies to hepatitis B surface antigen. Proc Natl Acad Sci USA. 1982 January; 79 (2): 650-4.
5. Shin Y W, Ryoo K H, Hong K W, Chang K H, Choi J S, So M, Kim P K, Park J Y, Bong K T, Kim S H. Human monoclonal antibody against Hepatitis B virus surface antigen (HbsAg). Antiviral Res. 2007 August; 75 (2): 113-20.
6. Wands J R. Zurawski V R Jr. High affinity monoclonal antibodies to hepatitis B surface antigen (HbsAg) produced by somatic cell hybrids. Gastroenterology. 1981 February; 80(2): 225-32.
7. Falero G. RodrAguez l, Sarracent J. Otero A J, RodrAguez B L, Rojas A, Ochoa E. Generation of murine triomas secreting bi-specific monoclonal antibodies that recognize HbsAG ad and ay subtypes. Hybridoma. 1992 December; 11 (6):815-23.
8. Shearer M H, Sureau C, Dunbar B, Kennedy R C. Structural characterization of viral neutralizing monoclonal antibodies to hepatitis B surface antigen. Mol immunol. 1998 December; 35(18):1149-60.
9. Maeda F, Nagatsuka Y, lhara S, Aotsuka S, Ono Y, Inoko H, Takekoshi M. Bacterial expression of a human recombinant monoclonal antibody fab fragment against hepatitis B surface antigen. J Med. Virol. 1999 August; 58(4): 338-45.

10. Lohman K L, Kieber-Emmons T, Kennedy R C. Molecular characterization and structural modeling of immunoglobulin variable regions form murine monoclonal antibodies specific for hepatitis B virus surface antigen. Mol. Immunol. 1993 October; 30(14):1295-306.
11. Heijtink R A, Kruining J, van Bergen P, de Rave S, van Hattum J. Schutten M, Osterhaus A D. Characterization of a human monoclonal antibody obtained after immunization with plasma vaccine and a booster with recombinant-DNA hepatitis B vaccine. J Med. Virol. 2002 March; 66(3):304-11.
12. Yano A, Maeda F, Takekoshi M. Transgenic tobacco cells producing the human monoclonal antibody to hepatitis B virus surface antigen. J Med. Virol. 2004 June; 73(2):208-15.
13. Desgranges C. Paire J, Pichoud C, Souche S, Frommel D, Trepo C. High affinity human monoclonal antibodies directed against hepatitis B surface antigen. J Virol Methods. 1987 July; 16 (4):281-92.
14. Ryu C J, Padlan E A, Jin B R, Yoo O J, Hong H J. A humanized antibody with specificity for hepatitis B surface antigen. Hum Antibodies Hybridomas. 1996; 7(3): 113-22.
15. Eren R. Lubin l, Terkieltaub D, Ben-Moshe O, Zauberman A, Uhlmann R, Tzahor T, Moss S, llan E, Shouval D, Galun E, Daudi N, Marcus H, Reisner Y, Dagan S. Human monoclonal antibodies specific to hepatitis B virus generated in a human/mouse radiation chimera: the Trimera system. Immunology. 1998 February; 93(2):154-612.
16. Morrison S L, Johnson M J, Herzenberg L A, Oi V T. Chimeric human antibody molecules; mouse antigen-binding domains with human constant region domains. Proc Natl Acad Sci USA. 1984 November; 81(21):6851-5.
17. Bose B, Khanna N, Acharys S K, Sinha S. High affinity mouse—human chimeric Feb against hepatitis B surface antigen. World J Gastroenterol. 2005 Dec. 28; 11(48); 7569-78.
18. Bose B, Khanna N, Acharya S K, Sinha S. Generation and characterization of a high-affinity chimeric antibody against hepatitis B surface antigen. Biotechnol Appl Biochem. 2006 February; 43(Pt2):93-101.
19. Khazaeli M B, Saleh M N, Liu T P, Meredith R F, Wheeler R H, Baker T S, King Secher D, Allen L, Rogers K, et al. Pharmacokinetics and immune response of 131l-chimeric mouse/human B72.3 (human gamma 4) monoclonal antibody in humans. Cancer Res. 1991 Oct. 15; 51 (20): 5461-6

OBJECTS OF THE INVENTION

The object of the invention is to generate a recombinant humanized antibody fragment (scFv) against hepatitis B surface antigen.

Other object is to develop a humanized recombinant antibody fragment which can bind to hepatitis B surface antigen with high affinity and specificity.

Another object is to produce a recombinant humanized antibody fragment (scFv) which would have less immunogenicity as compared to the mouse monoclonal.

Yet another object to produce a recombinant humanized antibody fragment (scFv) which would be more suitable for in-vivo use in humans.

Other objective is to generate anti-HBsAg humanized antibody which can be safer and cheaper alternative Further object is to develop the recombinant molecule which can also be used with/without any modification/in combination with other molecules for generation of complete full length antibody, bispecific antibodies and diabodies or any other modification of a protein molecule with containing the described humanized antibody fragment (scFv).

Yet another object is also to develop immuno-conjugates, like conjugated with enzymes, ligands, receptors, drugs, radio isotopes, toxins or any other large or small molecule for in-vivo or in-vitro use.

BRIEF DESCRIPTION OF THE ACCOMPANYING DRAWINGS

FIG. 1: Shows Schematic representation of generation of single chain variable fragment.

FIG. 2: Shows Schematic representation of steps involved in overlap PCR that was used to link gene segments.

FIG. 3: Demonstrates (a) SDS PAGE analysis of soluble antibody fragment (scFv) expressed in non-suppressor strain of *E. coli* HB2151. Lane IN AT51 and M represent the periplasmic extract of IPTG induced AT51 clone and protein molecular weight marker respectively.

(b) Western blot analysis of soluble scFv. HB represents the induced periplasmic extract of untransformed HB2151 cells. Antibody fragment was detected using anti E tag antibody followed by anti mouse HRP conjugate.

FIG. 4: Demonstrates Antigen binding analysis of soluble recombinant antibody fragment. Similar dilution of periplasmic extract of various clones was used in the experiment. 5S hybridoma soup was used as positive control and periplasmic extract of untransformed HB2151 was used as negative control. AT51 clone was used for further experiments.

FIG. 5: Demonstrates ELISA with different dilutions of soluble antibody fragment (scFv). Soluble scFv was used in different dilution to bind to the HBsAg coated on ELISA plate (250 ng/well) and bound scFv was detected using anti E tag antibody followed by anti mouse HRP conjugate antibody. Periplasmic extract of untransformed HB2151 cells were used as negative control for the experiment and its binding to the antigen was considered as base line reading for this experiment.

FIG. 6: Shows effect of urea on antibody binding, analyzed by ELISA for humanized scFv, mouse scFv and the mouse monoclonal 5S.

FIG. 7: Shows effects of DMSO, which destabilizes antigen-antibody interactions, which was checked by ELISA.

FIG. 8: Shows effect of NaCl on antigen interaction, which was analyzed by ELISA.

FIG. 9. Shows Antigen antibody analysis at different pH by ELISA.

FIG. 10: Demonstrates of average dissociation constant ($K_D$) of 5S mouse monoclonal antibody and humanized scFv. Antibodies were incubated with different amount of the antigen overnight to reach the equilibrium and free antibodies were determined by ELISA with 20 minutes of incubation. Data points were fitted to the equation $A_0/(A_0-A)=K_D[Ag]+1$, where $A_0$=absorbance when the antibody was incubated without antigen, A=absorbance corresponding to free antibody after incubation with antigen and [Ag]=free antigen concentration which is equal to the antigen taken for experiment considering a pseudo first order reaction. As calculated from the slope of the straight lines, the $K_D$ values for humanized scFv and the mouse monoclonal were 1.206 nM ($R^2$=0.9872) and 1.114 nM ($R^2$=0.9909), respectively.

FIG. 11: Alignment of 5S VH sequence (a) and 5S VL sequence (b) with the most homologous human consensus sequence (VH subgroup I) and (VL$_K$ subgroup II) respectively. The mismatched residues are marked in single letter code. CDR regions are marked by box. The sequences of humanized VH and VL are also aligned with their corresponding chains.

FIG. 12: Nucleotide sequence of humanized anti-HBs-scFv. Corresponding amino acid sequence is marked in single letter code. The linker peptide is underlined.

DETAILED DESCRIPTION OF THE INVENTION

At the Outset

In order to make the humanized antibody fragment (scFv), the inventors have adopted a recombinant approach, where individual $V_H$ and $V_L$ have been linked by flexible linker and cloned in a phagemid vector. For the humanization, non-human like framework residues in the 5S-scFv were selected by aligning them with best homologous human antibody sequence/human consensus sequence. Selected non human like residues were subsequently mutated to human residues by site-directed mutagenesis. In the process of humanization, apart from the residues at low risk positions, several minimal positional residues (high risk positions) were mutated without affecting binding affinity. Interestingly, inventors also did fine tuning of the "vernier zone" residue to get close to the human sequence without and structural constraint. The resulting humanized scFv has generated novel inter/intra-chain bonding interactions as compared to mouse scFv. This humanized scFv shows high binding affinity and epitope specificity to the HbsAg inspite of the twenty eight altered amino acids. The humanized antibody fragment also has dissociation constant in nano molar range equivalent to that of the original mouse monoclonal.

This recombinant antibody fragment also maintained antigen binding in the presence of various destabilizing agents like 3M NaCl, 30% DMSO, 8M urea and extreme pH. This high affinity humanized scFv provides a platform/basis for the development of therapeutic molecules which can be safely utilized for the treatment of hepatitis B.

At the outset of the description that follows, it is to be understood that the ensuing description only illustrates a particular form of this invention. However, such a particular dog is only an exemplary embodiment and is not intended to be taken restrictively to imply any limitation on the scope of the present invention.

There are many well known methods to generate humanized antibody. However, every recombinant humanized antibody is unique in nature, if and only if (a) its molecular structure as defined by the amino acid sequence is unique (b) has unique biological function as defined by specificity and affinity for the target antigen. The recombinant molecule of this invention is unique as no other molecule matches the structure and properties of this molecule. This novel molecule can be generated by many other well documented strategies too.

Other recombinant molecule may have the same function as they bind the hepatitis to surface antigen but each molecule with different sequences has unique binding characteristics in terms of epitope specificity i.e. the precise sequence of antigen it binds to and the molecular interactions for doing the same and affinity.

Here, the inventors generated a recombinant humanized antibody fragment (scFv) composed of humanized $V_H$ (variable region of heavy chain) and humanized $V_L$ (variable region of light chain), which binds to hepatitis B surface antigen with high affinity. Only the antibody fragment and not the individual $V_L$ and $V_H$ can bind to hepatitis B surface antigen thus be useful for virus neutralization.

Inventors have used the antibody genes from a mouse monoclonal (5S) for generation of recombinant antibody fragment (scFv) against hepatitis B surface antigen. This antibody binds to the immunodominant 'a' epitope of the hepatitis B surface antigen and found to be protective in a surrogate in-vitro assay. This mouse monoclonal was generated using existing protocol for generation of hybridomas. However, this mouse monoclonal can not be used directly in human subjects, as it will induce human anti mouse antibody (HAMA) response. To reduce the immunogenicity of the antibody, inventors have generated a recombinant humanized antibody fragment that retains the high affinity and specificity for HBsAg. Variable region genes ($V_H$ and $V_L$) of the mouse monoclonal (5S) were amplified by reverse transcription (RT) followed by polymerase chain reaction (PCR). Mouse $V_L$ and $V_H$ were linked with a flexible linker to generate single chain variable fragment by overlap PCR. Phagemid vector pCANTAB 5E (Amersham Biosceinces) was used to express the soluble scFv in the periplasmic space of E. coli (HB2151).

In order to prepare a humanized scFv, we constructed a molecular model of scFv by web based modeling software to analyze the structural significance of each and every residue. We selected a human antibody sequence from database that shows the highest homology of amino acid sequence to the mouse $V_H$ and $V_L$. The immunogenic (mouse) framework residues were identified that differed from human framework residues in highly homologous human $V_H$ and $V_L$ sequences. The selected residues were subsequently mutated to human residue by site directed mutagenesis. We preserved a few mouse residues based on the information of the possible interaction of these residues with other framework residues observed in a structural model. The selected human antibody sequence contains some unusual residues at certain positions, but the mouse scFv actually has a residue much more typical of human sequences than the selected human antibody. At these positions, we therefore chose to use the parent murine antibody residue rather the selected human antibody residue in the humanized antibody to make the antibody more generically human. These criteria allowed the selection of all amino acids in the humanized scFv as coming from either selected human antibody or form human consensus sequence.

After initial screening using the phage display system, the humanized scFv was expressed in soluble form in the periplasm of E. coli (HB2151). The resulting humanized antibody fragment showed high binding to HBsAg and competitive ELISA confirmed that it binds to the same epitope as that of the original mouse monoclonal (5S). The apparent dissociation constant ($K_D$) of the humanized antibody fragment was found to be very close to that of the original mouse monoclonal (1.206 nM ($R^2$=0.9872).

This humanized antibody fragment can be further manipulated to generate the complete humanized IgG derivatives by fusing the human heavy and light chain constant domains. Therefore this humanized antibody fragment, which has unique mouse CDRs and human like framework regions can be the starting material for generation of a therapeutically functional full length recombinant antibody which can be utilized for passive therapy in case of HBV infection. Being a humanized antibody, it is expected to be least immunogenic than a chimeric/mouse antibody and a generated by recombinant means it can be safer and cheaper that the currently used human polyclonal antibody.

Cloning and Generation of the Recombinant Antibody Fragment (scFv):

The strategy for generation of the recombinant antibody fragment is shown in FIG. 1. The variable region genes of 5S hybridoma were amplified by reverse transcription followed by PCR. Primers used for all reverse transcription and PCRs are listed in Table 1. Total RNA was extracted from 5S hybridoma cells using standard protocol and cDNA was generated by reverse transcription using a primer against 3' conserved region of antibody variable region genes. PCR amplification of variable region of heavy chain ($V_H$) and light chain ($V_L$) was performed with degenerate primers for 35 cycles of 94° C. for 1 min, 50° C. for 1 min and 72° C. for 2 min; followed by a final extension at 72° C. for 10 min. PCR amplified products were resolved in 1.5% agarose gel and respective bands were eluted out using the standard protocol. For the construction of scFv gene, $V_H$, $V_L$ and linker fragments were joined by overlap PCR. The strategy for overlap PCR is shown here in FIG. 2. Initially $V_H$ and linker fragments were taken in equivalent molar ratio and linked by PCR (20 cycles, 50° C. annealing) with out using any primer. The PCR product was diluted 10 times and amplified by PCR relation (35 cycles, 50° C. annealing) using external primers (46 and 50). Similar protocol was used to join $V_L$ and linker fragment. Both the $V_H$-linker and linker-$V_L$ fragments were resolved on 1.5% agarose gel and specific bands were cluted out. These two eluted fragments were linked by another overlap PCR using primers (49 and 45). Assembled scFv was then digested with Not1 and Sfi 1 and ligated into the phagemid vecot pCANTAB 5E, which includes the 'E tag' for detection and purification purposes. XL-1-Blue cells were transformed with the resulting phagemid pCANTAB-5S-scFv using a standard chemical (CaCl$_2$) transformation protocol. Transformed cells were grown on Ampicillin-Agar plates. Colonies were picked up after overnight incubation and screened for presence of the insert by PCR screening and restriction digestion.

Figure 4:
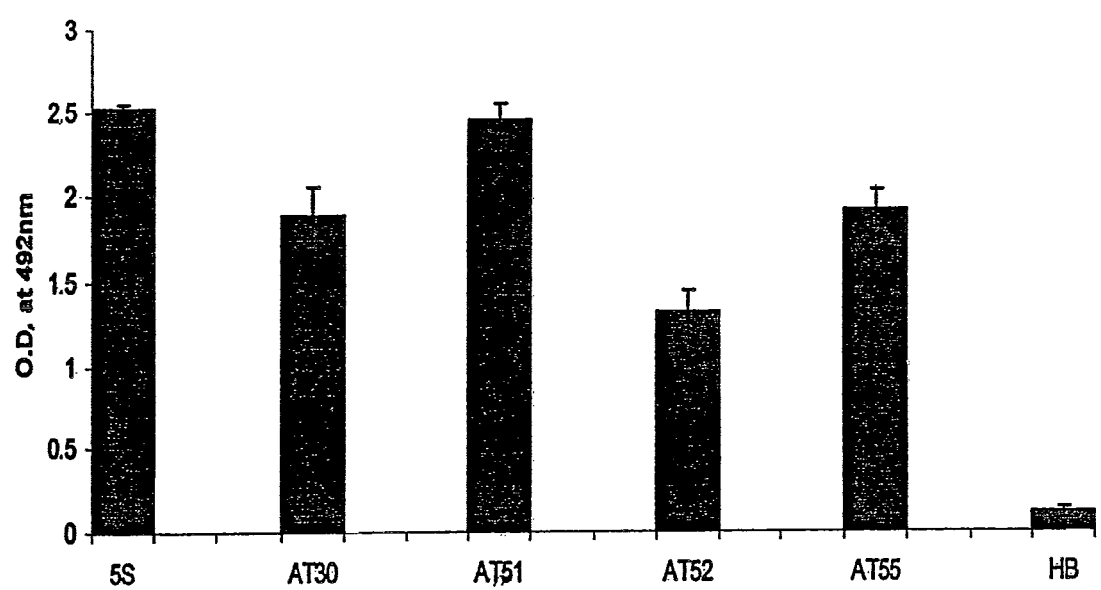

Selection and Expression of Antigen Binding Antibody Fragment:

It is well known that truncation and mutations can be generated due to PCR and the cloning process. Therefore, cloned scFv library was screened by bio-panning over antigen coated ELISA plate. After three rounds of enrichment, selected clones were used to prepare phage antibody and antigen-binding clones were detected by phage-ELISA Clone AT51 which showed the maximum absorbance has been used for soluble expression by inducing HB2151$^{NaI}$ culture with 1 mM IPTG for 6 h at 27° C. After induction, a band with molecular weight of ~29 kDa, corresponding to scFv was detected in the periplasmic extract of AT51 infected HB2151$^{Na1}$ cells (FIG. 3a), this was further confirmed by western blot using HRP/anti-E tag mouse antibody (FIG. 3b). Binding of the recombinant antibody fragment was detected by solid phase ELISA and the result is shown in FIG. 4.

Molecular Modeling of Recombinant Antibody Fragment:

In order to study the importance of the framework residues that could influence CDR conformation, and thus Ag-binding affinity and/or activity. Molecular model of the scFv was constructed using WAM, web based antibody modeler. The model of humanized scFv was further constructed by WAM. Single residue changes were made manually in the resulting model and then subjected to energy minimization using the software provided with the Swiss PDB Viewer program. The compatibility of all the substitutions in framework regions with remaining structure was analyzed. We superimposed the models of mouse and humanized scFv and systematically compared each and every residue. The quality of molecular models of mouse 5S-scFv and humanized scFv was determined by examining the distribution of amino acids residues in the Ramachandran plot.

Humanization of the Antibody Fragment (5S-scFv):

The amino acid sequences of $V_H$ of 5S-scFv were independently aligned against the entire repertoire of human antibody sequences contained in the Gene Bank database using BLAST search. The inventors considered human consensus sequences and best homologous human antibody sequences (depending upon the sequence similarity) for humanization of 5S-scFv, as it was showing highest homology with the human consensus sequences tabulated in the database. The human antibodies chosen also had similarity to 5S-scFv in the sequence of the CDRs and had the same loop length (except CRD H3), which further indicates that they belongs to a similar structural group and perhaps have a similar canonical structure of CDR loops.

In order to humanize the recombinant mouse antibody fragment, non-human like framework residues in the 5S-scFv were selected by aligning them with best homologous human antibody sequence/human consensus sequence. Among the selected residues, only those were mutated which were not shown in any structural discrepancy with in the context of molecular model of 5S-scFv. Selected non-human like residues were subsequently mutated to human residues using the pCABTAB 5E vector containing mouse 5S-scFv DNA with the QuickChange Multi Site-Directed Mutagenesis kit (Stratagene) according to the manufacture's instructions. All the primers used in site-directed mutagenesis are listed in Table No. 2A and 2B. Individual colonies of mutant clones were sequenced to confirm the presence of the correct mutations.

Figure 5:
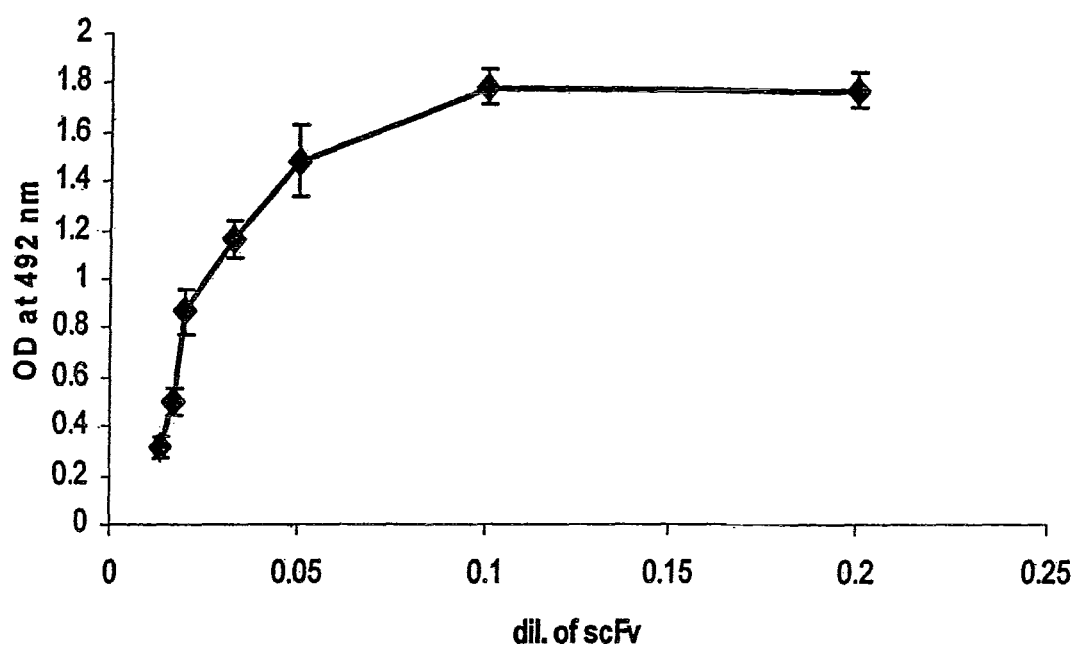
Figure 6:
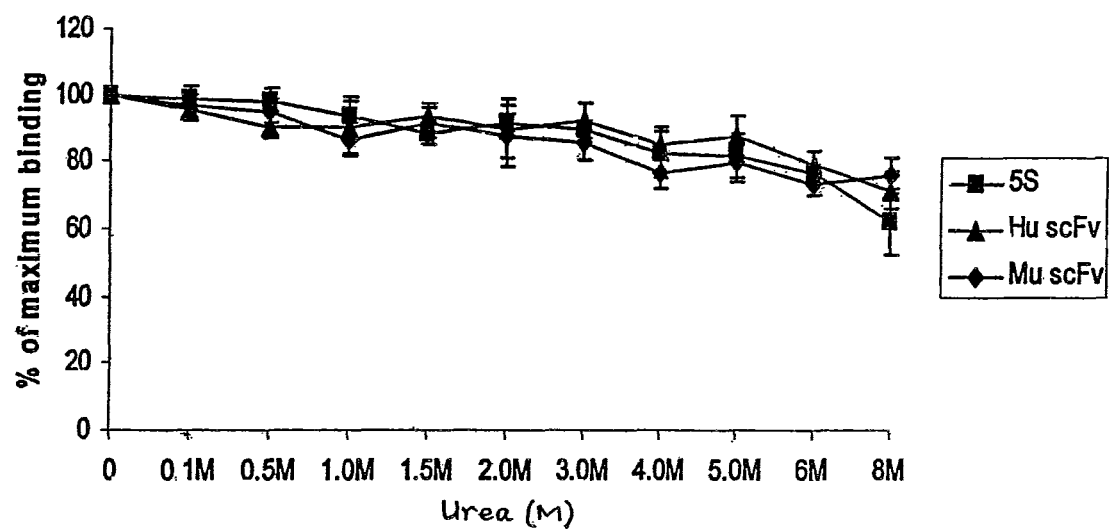
Figure 7:
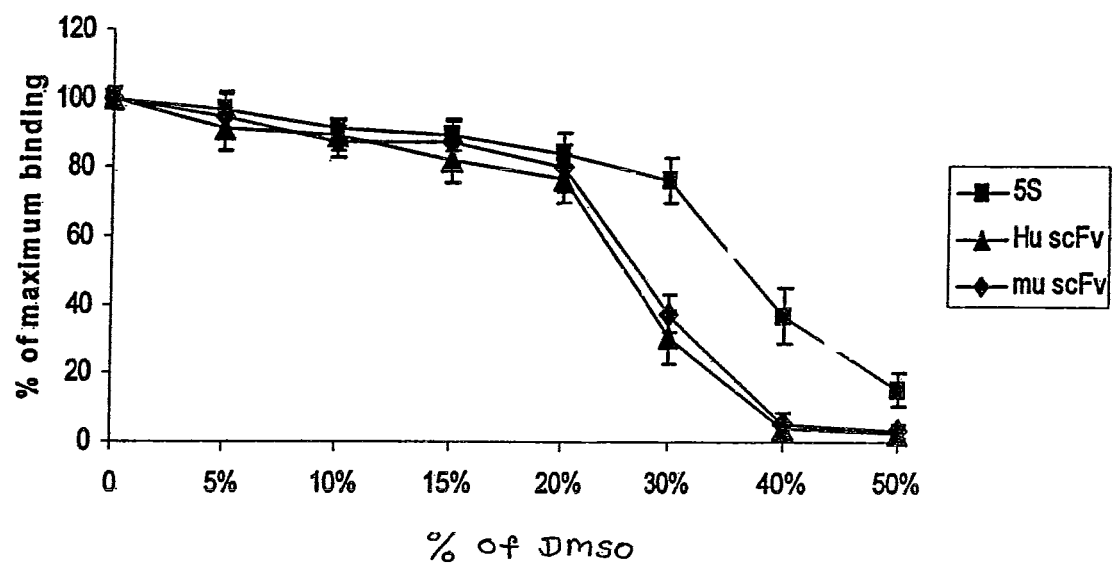
Figure 8:
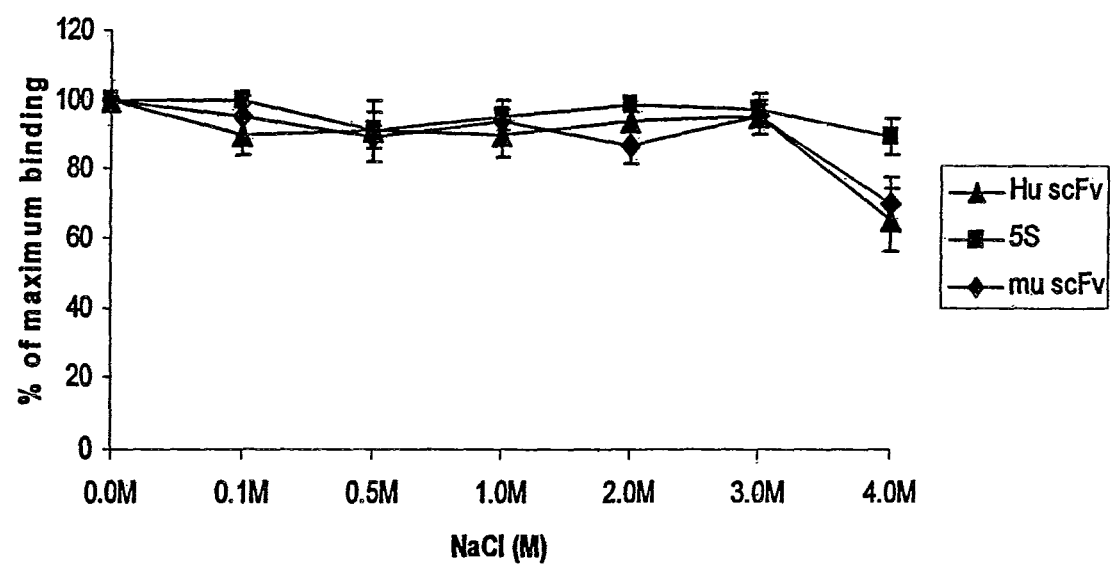
Figure 9:
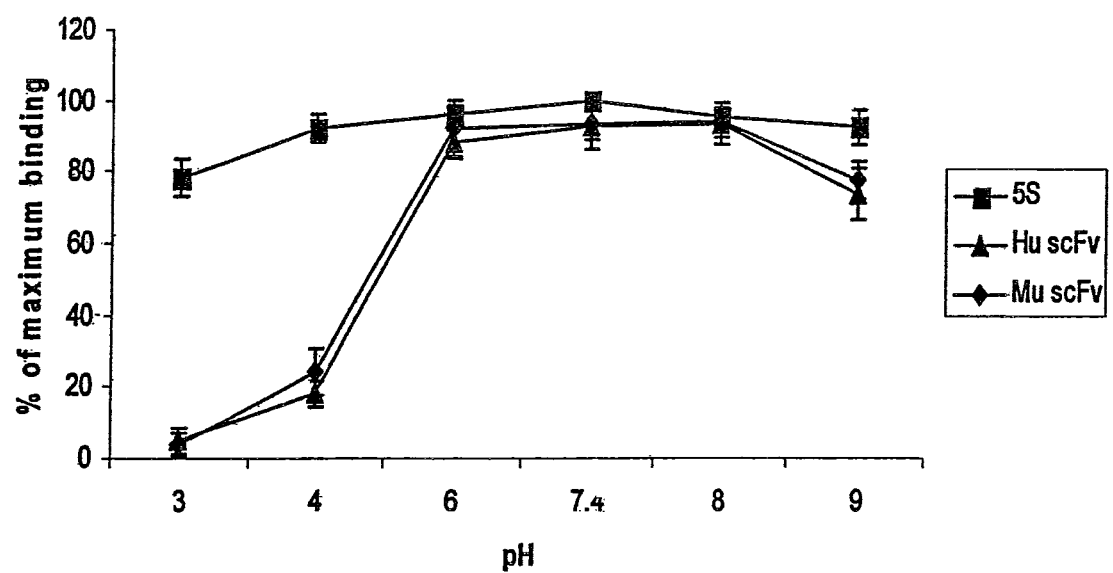

Binding Properties of the Humanized Antibody Fragment:

Antigen binding assay for the humanized antibody fragment was done by solid phage ELISA (FIG. 5). As shown in the FIG. 5, the binding of humanized scFv increase with the increasing amount of the humanized scFv and reaching a saturation level as expected in the antigen-antibody interactions. Further characterization of binding strength and conformational stability of both the molecules was evaluated by ELISA in the presence of different concentration of various destabilizing agents like urea, DMSO, NaCl and at different pH. As shown in FIGS. 6 and 7 both mousse scFv and the humanized scFv bind to the antigen in higher concentration of urea and DMSO like mouse monoclonal (5S), indicating strong and very stable interaction between the antigen and antibodies. Similar results were obtained in presence of different concentration of NaCl and at extrement of pH as shown in FIGS. 8 and 9.

Figure 10:
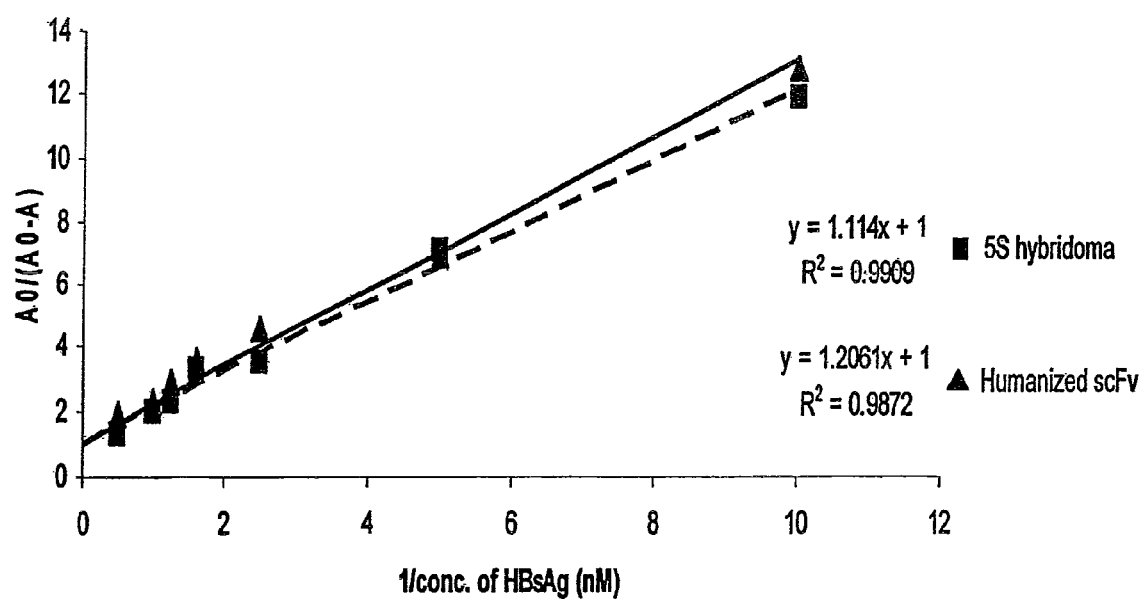

Dissociation Constant of the Mouse 5S-scFv and Humanized scFv:

Dissociation constant $K_D$, for mouse 5S-scFv and the humanized scFv were determined by the standard ELISA based method. To meet the basic assumptions of the method, antigen was taken in excess to the antibody and all experiments were performed within the range of dilutions of the antibody, where absorbance in the ELISA changes linearly with dilution. As the interaction between coated antigen with the free/bound antibody can shift the equilibrium, we had incubated the overnight equilibrated antigen-antibody mixture, in antigen coated plate only for 20 min. This time is sufficient enough to measure the free antibody without causing considerable shift in the equilibrium (data not shown). The $K_D$ values can be calculated from the slope of the straight lines in FIG. 10. The experiments show that the humanization process did not undermine the binding affinity and conformational stability of humanized scFv. The humanized scFv has shown similar binding and kinetic properties as of the present murine monoclonal.

Inventive Steps:
1. Amplification of the variable region genes ($V_H$ and $V_L$) of the anti-HBs mouse monoclonal 5S by reverse transcription (RT) followed by polymerase chain in reaction (PCR). RNA isolated form 5S hybridoma was used as the source of $V_H$ and $V_L$ genes.
2. Generation of recombinant antibody fragment (scFv) by joining $V_L$ and $V_H$ with a flexible linker by overlap PCR.
3. Recombinant antibody fragment (scFv) was cloned into pCANTAB 5E phagemid vector (Amersham Biosciences) for expression of phage antibody (E. coli; XL1-blue, suppressor strain) as well as soluble scFv (E. coli; HB2151, nonsuppressor strain).
4. Selection of best homologous human antibody sequence from the database in order to humanize the recombinant mouse scFv.
5. Structural significance of each and every residue of mouse scFv was analyzed with the help of computer aided molecular modeling.
6. Selected mouse frame work residues were subsequently mutated to human residue by site directed mutagenesis.
7. Binding analysis and affinity measurement of recombinant humanized antibody fragment (scFv) was done by various ELISA based methods.

TABLE 1

List of primes used in reverse transcription and PCR

| | |
|---|---|
| Light chain 3' (45) | 5' -TCG ACT TGC GCC CGC CCG TTT KAK YTC CAR CTT KGT SCC-3' |
| Heavy chain 3' primer (47) | 5'-TGA RGA GAC RGT GAC TGA RGT-3' |
| Light chain 5' primer (44) | 5' ATT GTG ATG ACC CAG ACT-3' |
| Heavy chain 5' primer (46) | 5' GCA ACT GCG GCC CAG CCG GCC ATG GCC GAG GTG CAG CTK CAG CAG-3' |
| Linker template (48) | 5' GGT GGT GGT GGG AGC GGT GGT GGC ACT GGC GGC GGC GGA TCT-3' |
| Linker template 5' (49) | 5' TCA GTC ACY GTC TCY TCA GGT GGT GGT GGG AGC-3' |
| Linker template 3' (50) | 5' GT CTG GGT CAT CAC AAT AGA TCC GCC GCC GCC-3' |

Present invention deals with a high affinity humanized antibody fragment specific for hepatitis B surface antigen. This recombinant molecule has unique inter/intra chain bonding interaction as it has several altered amino acid residues form the original mouse (5S) antibody and its chimeric Fab from (Patent Application #2704/DEL/2006). Interestingly, inventors also did fine tuning of the "vernier zone" residue to get close to the human sequence without any structural constraint. Vernier residues are known for making direct contact with the antigen and/or for making $V_H/V_L$ domain interface. This recombinant humanized scFv is unique molecule in terms of antigen contact and structural base from any other known anti HbsAg antibody available in the literature.

Currently, Hepatitis B immune globulin (HBIG), collected from the blood of hyper immune human donors, is used for the post-exposure prophylaxis in cases of accidental needle stick injuries, liver transplant patients and for the prevention of vertical transfer of HBV infection form mother to child. This blood-derived product is not manufactured in India. However, such blood-derived products are costly and can cause cross-contamination. Therefore a recombinant antibody to HbsAg can be suitable alternatives to such a practice. Inventors have developed a mouse monoclonal antibody (5S) against the 'a' epitope of the hepatitis B surface antigen (HBsAg). However such mouse antibodies often induce a significant human anti mouse antibody (HAMA) response when administered to patients and thus limiting their potential use for human therapy, especially when repeated administration is necessary.

For therapeutic purposes it may be necessary to fully humanize a murine antibody by altering the variable domain to make them human like. It is well established that humanization of mouse antibody is desirable to reduce its potential product immunogenicity. However humanization is practical only if it does not reduce or destroy the binding affinity of antibody. Humanized antibodies are safer for therapeutic uses and currently several such humanized antibodies are in clinical uses for various diseases. Although some chimeric antibodies are in clinical use. It is worth noting that most of the antibodies in phase 1, II clinical trials today are humanized antibodies.

The anti-HBsAg humanized antibody fragment invented can be further manipulated and can be utilized for passive therapy in case of HBV infection. The humanized antibody is safer and cheaper alternative and more suitable for therapeutic use.

TABLE 2A

List of primers used in site-directed mutagenesis of VH gene fragment

| Position | Mutation | Primer Sequence |
|---|---|---|
| H5 | (Q-V) | 5'-G GTG CAG CTG CAG GTG CCC GGG GCT GAG-3' |
| H7 | (P-S) | 5'-G CAG CTG CAG CAG AGC GGG GCT GAG C-3' |
| H11 | (L-V) | 5'-GGG GCT GAG GTG GCG ACG CCT GG-3' |
| H13 | (T-K) | 5'-GCT GAG CTG GCG AAG CCT GGG GCC TC-3' |
| H18 | (L-V) | 5'-CT GGG GCC TCA GTG AAG ATG TCC TGC AAG-3' |
| H20 | (M-V) | 5'-G GCC TCA GTG AAG GTG TCC TGC AAG G-3' |
| H38 | (K-R) | 5-CAC TGG GTA CGG CAG ACA CCT GG-3' |
| H40 | (T-A) | 5'-G GTA CGG CAG GCA CCT GGA CGG GG-3' |
| H43 | (R-Q) | 5'-G GCA CCT GGA CAG GGC CTG GAA TG-3' |

TABLE 2A-continued

List of primers used in site-directed mutagenesis of VH gene fragment

| Position | Mutation | Primer Sequence |
|---|---|---|
| H75 | (S-T) | 5'-CT GCA GAC AAA TCC ACC AGC ACA GCC TAT TTG C-3' |
| H81 | (H-E) | 5'-C TCC AAC ACA GCC TAT TTG GAA CTC AAC AGC CTG ACA TC-3' |
| H82a | (N-S) | 5'-CC TAT TTG GAA CTC AGC AGC CTG ACA TCT G-3' |
| H83 | (T-R) | 5'-C AGC AGC CTG AGA TCT GAG GAC TC-3' |
| H87 | (S-T) | 5'-G ACA TCT GAG GAC ACC GCG GTC TAT TAC TG-3' |
| H108 | (S-L) | 5'-GGT CAA GGA ACC CTG GTC ACT GTC TCT TC-3' |

TABLE 2B

List of primers used in site-directed mutagenesis of VL gene fragment

| Position | Mutation | Primer Sequence |
|---|---|---|
| L7 | (T-S) | 5'-GTG ATG ACC CAG AGT_CCA CTC TCC C-3' |
| L14 | (S-T) | 5'-CC CTG CCT GTC ACC_CTT GGA GAT CAA GC-3' |

TABLE 2B-continued

List of primers used in site-directed mutagenesis of VL gene fragment

| Position | Mutation | Primer Sequence |
|---|---|---|
| L15 | (L-P) | 5'-C CTG CCT GTC ACC CCG_GGA GAA CAA GCC T-3' |
| L17 | (D-E) | 5'-CT GTC ACC CTT GGA GAA_CAA GCC TCC ATC TC-3' |
| L18 | (Q-P) | 5'-C ACC CCG GGA GAA CCG_GCC TCC ATC TCT T-3' |
| L36 | (H-Y) | 5'-CC TAT TTG GAA TGG TAC_CTG CAG AAA CCA G-3' |
| L45 | (K-Q) | 5'-GGC CAG TCT CCA CAG CTC CTG ATC TAC-3' |
| L70 | (E-D) | 5'-GT GGA TCA GGG ACA GAT TTC ACA CTC AAG-3' |
| L83 | (L-V) | 5'-GGA GGC ACC AAG GTG GAA CTC AAA CGG GC-3' |
| L87 | (F-Y) | 5'-GAT GTG GGA GTT TAT TAC TGC TTT CAA CGT TC-3' |
| L100 | (G-Q) | 5'-G TGG ACG TTC GGT CAA GGC ACC AAG CTG-3' |
| L104 | (L-V) | 5'-GGA GGC ACC AAG GTG GAA CTC AAA CGG GC-3' |
| L106 | (L-I) | 5'-GC ACC AAG GTG GAA ATC AAA CGG GCG G-3' |

We claim:

1. A humanized antibody fragment which specifically binds to a Hepatitis B surface antigen (HBsAg) comprising:
    a human immunoglobulin framework region comprising a first amino acid sequence selected from the group consisting of SEQ ID NOs.: 7-14; and
    comprising six non-human complementarity determining regions (CDRs) having the amino acid sequences of SEQ ID NOs.: 1-6;

wherein the humanized antibody fragment is folded in a manner to bind to the HBsAg.

2. A humanized antibody fragment which specifically binds to Hepatitis B surface antigen (HBsAg) comprising a human immunoglobulin framework comprising a non-human amino acid sequence containing at least one mutation at a position selected from the group consisting of: 7L, 14L, 15L, 17L, 18L, 36L, 45L, 70L, 83L, 87L, 100L, 104L, 106L, 5H, 7H, 11H, 13H, 20H, 38H, 40H, 43H, 75H, 81H, 82aH, 83H, 87H, and 108H and non-human complementarity determining regions (CDRs); wherein the CDRs comprise the amino acid sequences of SEQ ID NOs.: 1-6; and wherein the humanized antibody fragment is folded in a manner to bind to the HBsAg.

3. The humanized antibody fragment according to claim 2, wherein the mutation is at position 7L and the framework region further comprises a plurality of mutations at positions 14L, 15L, 17L, 18L, 36L, 45L, 70L, 83L, 87L, 100L, 104L, 106L, 5H, 7H, 11H, 13H, 18H, 20H, 38H, 40H, 43H, 75H, 81H, 82aH, 83H, 87H, and 108H.

4. A humanized antibody fragment which specifically binds to a Hepatitis B surface antigen (HBsAg) comprising:
   a human immunoglobulin framework region comprising a first amino acid sequence of SEQ ID NO.: 7, and where the framework region further comprises amino acid sequences SEQ ID NOs.: 8-14; and
   comprising six non-human complementarity determining regions (CDRs) having the amino acid sequences of SEQ ID NOs.: 1-6;
   wherein the humanized antibody fragment is folded in a manner to bind to the HBsAg.

5. The humanized antibody fragment according to claim 4, wherein the humanized antibody fragment binds to recombinant HBsAg and HBsAg derived from serum of a recovered patient with an apparent dissociation constant (Kp) of about 1.20 nm or better affinity.

6. The humanized antibody fragment according to claim 1, wherein the humanized antibody fragment binds to recombinant HBsAg and HBsAg derived from serum of a recovered patient in the presence of 4M urea, 2M NaCl, 20% DMSO and at a pH range 6 to 9.

7. The humanized antibody fragment according to claim 1, wherein the framework region has 100% homology to a chosen human consensus framework sequence; and further comprising a heavy chain having 91% homology to a human subgroup framework sequence.

8. The humanized antibody fragment according to claim 1, wherein the CDR can be used for generating a full length antibody with a different effector function.

9. The humanized antibody fragment according to claim 1, wherein the antibody fragment can be used as a diagnostic reagent for detection of Hepatitis B surface antigen (HBsAg).

10. A diagnostic reagent comprising the humanized antibody fragment as claimed in claim 1.

11. The humanized antibody fragment according to claim 2, wherein the human immunoglobulin framework comprising a non-human amino acid sequence contains at least a second mutation, at position 18H.

* * * * *